United States Patent [19]

Fukazawa et al.

[11] Patent Number: 5,047,545

[45] Date of Patent: Sep. 10, 1991

[54] 2-ALKOXYCARBONYL-4-(4-PYRIDYL)CYCLOHEXANONES AND PROCESS FOR PREPARING THEM

[75] Inventors: Nobuyuki Fukazawa; Hiroyuki Yamashita, both of Kanagawa, Japan

[73] Assignee: Mitsui Toatsu Chemicals, Inc., Tokyo, Japan

[21] Appl. No.: 300,179

[22] Filed: Jan. 23, 1989

Related U.S. Application Data

[63] Continuation of Ser. No. 23,104, Mar. 3, 1987, abandoned.

[51] Int. Cl.$^5$ ............................................. C07D 217/26
[52] U.S. Cl. ................................................... 546/342
[58] Field of Search ........................................ 546/342

[56] References Cited

FOREIGN PATENT DOCUMENTS 2162178 1/1986 United Kingdom ................ 546/112

OTHER PUBLICATIONS

Windholz et al, *The Merck Index*, 1976, p. ONR-23.
Lochte et al., *JACS*, Sep. 20, 1953, pp. 4477-4481.
*Modern Synthetic Reactions*, "The Organic Chemistry Monograph Series", H. House, 2nd Edition, pp. 740-743 (1972).
*Isoquinolines* Part 1, G. Grethe, pp. 252-253 (1981).
Chemical Abstracts, vol. 76, No. 23, p. 450 (1972) Abstract No. 140,475c.
*Tetrahedron*, The Knoevenagel Reaction of Malononitrile with Some Cyclic . . . , J. L. van Der Baan & F. Bickelhaupt, vol. 30, pp. 2447-2453 (1974).

*Primary Examiner*—C. Warren Ivy
*Assistant Examiner*—Zinna Northington-Davis
*Attorney, Agent, or Firm*—Browdy and Neimark

[57] ABSTRACT

2-Methoxycarbonyl-4-(4-pyridyl)cyclohexanone of the present invention is an important intermediate for preparing isoquinoline derivatives which are useful as medicines, particularly as heart medicines.

2 Claims, No Drawings

2-ALKOXYCARBONYL-4-(4-PYRIDYL)CYCLOHEXANONES AND PROCESS FOR PREPARING THEM

This application is a continuation of application Ser. No. 023,104, filed Mar. 3, 1987, now abandoned.

BACKGROUND OF THE INVENTION

1. Field of the Invention

The present invention relates to 2-alkoxycarbonyl-4-(4-pyridyl)cyclohexanones and a process for preparing them. 2-Alkoxycarbonyl-4-(4-pyridyl)cyclohexanones are important intermediates of agricultural chemicals and medicines, in particular for preparing isoquinoline derivatives which are in turn useful as medicines.

2. Description of the Prior Art

2-Carboxylic acids of cyclohexanone derivatives having a substituent at 4-position have been known: see D. Y. Curtin, J.A.C.S., 1960, 82, 2357. such carboxylic acids having a phenyl substituent at 4-position can be esterified to produce 2-alkoxycarbonyl-4-phenylcyclohexanones. However, 2-alkoxycarbonyl-4-(4-pyridyl)-cyclohexanones, which are objects of the present invention, have not been known at all.

According to the prior art referred to hereinabove, the 2-alkoxycarbonyl-4-phenylcyclohexanones are prepared by first providing 4-phenylcyclohexanones and then introducing a carboxyl group into 2-position.

Thus, if 2-alkoxycarbonyl-34-(4-pyridyl)cyclohexanones of the present invention are to be prepared according to the conventional technique, then 4-(4-pyridyl)cyclohexanones must be first provided. However, the 4-(4-pyridyl)cyclohexanones themselves are unknown compounds and, accordingly, this problem of preparing novel 2-alkoxycarbonyl-4-(4-pyridyl)cyclohexanones cannot be solved by application of the conventional process.

SUMMARY OF THE INVENTION

The present inventor has made great efforts to seek a process for preparing 2-alkoxycarbonyl-4-(4-pyridyl)-cyclohexanones which are useful as intermediates of agricultural chemicals and medicines, and particularly are important intermediates for producing isoquinoline derivatives that are themselves useful as medicines. As a result, the present inventor has found a process for preparing easily 2-alkoxycarbonyl-4-(4-pyridyl)cyclohexanones by Dieckmann condensation of 4-(4-pyridyl)pimelic acid esters and thus attained the present invention.

DESCRIPTION OF THE INVENTION

The process of the present invention will hereinbelow be described in more detail.

The process of the present invention is carried out according to the following reaction route:

[Structure (II): 4-pyridyl-CH$_2$CN] $\xrightarrow{\text{2CH}_2\text{=CHCO}_2\text{R}}_{\text{catalyst}}$ (II)

-continued

[Structure (III): 4-pyridyl-C(CN)(CH$_2$CH$_2$CO$_2$R)$_2$] $\xrightarrow[\text{(2) R—OH/acid}]{\text{(1) hydrochloric acid}}$ (III)

[Structure (I): 4-pyridyl-CH(CH$_2$CH$_2$CO$_2$R)$_2$] $\longrightarrow$ (I)

[Structure: 4-pyridyl-cyclohexanone with CO$_2$R]

In the reaction route R represents a methyl or ethyl group.

The reaction of the compound (II) with an acrylic acid ester may be carried out in an organic solvent or in the absence of any solvent at a temperature in the range from room temperature to 50° C. while using a base such as 1,8-diazabicyclo[5.4.0]-7-undecene as a catalyst to produce a compound of the general formula (III).

Then, the compound (II) is heated in hydrochloric acid. Thus, the hydrolysis of the cyano group and decarboxylation of the resulting carboxyl group are effected while at the same time R groups of the ester residues are hydrolyzed.

The thus obtained product can directly be esterified without being isolated to produce a 4-(4-pyridyl)-pimelic acid ester of the general formula (I).

The compound (I) may then be subjected to Dieckmann condensation to produce a 2-alkoxycarbonyl-4l-(4-pyridyl)cyclohexanone according to the present invention.

Various organic solvents may be used as a reaction solvent in the Dieckmann condensation. Preferred solvents are alcohols, benzene, toluene or tetrahydrofuran. Any temperature in the range from room temperature to the boiling point of the solvent used may be utilized, and high temperatures need not necessarily be employed.

Various bases may be utilized in the Dieckmann condensation, but sodium alkoxide or potassium tert-butoxide is preferred.

According to the present invention, there can be provided novel 2-alkoxycarbonyl-4-(4-pyridyl)cyclohexanones which are important intermediates of agricultural chemicals and medicines, in particular, for preparing isoquinoline derivatives useful as medicines.

The present invention will be more fully illustrated by the following non-limiting example.

In the example, only methyl ester of acrylic acid is shown, but the process of the present invention will be effected in a substantially similar manner with the ethyl ester of acrylic acid.

EXAMPLE (1) 4-Cyano-4-(4-pyridyl)pimelic acid methyl ester

To 10.4 g of methyl acrylate, there was added 0.2 g of 1,8-diazabicyclo[5.4.0]-7-undecene. Under ice-cooling, the mixture was maintained at 20° to 40° C. while stirring. A solution of 14.2 g of 4l-pyridylacetonitrile in 20.8 g of methyl acrylate was added. After 30 minutes, the water bath was removed and the reaction mixture was stirred at room temperature for additional one hour. Excess methyl acrylate was distilled off under reduced pressure. Purification by a silica gel column gave 35 g of 4-cyano-4l-(4-pyridyl)pimelic acid methyl ester as an oily material.

IR(Neat): 2950, 2230, 1740, 1590, 1430, 1200 cm$^{-1}$

NMR(100 MHz, CCl$_4$, δ): 8.6 (2H, m); 7.4 (2H, m); 3.58 (6H,s); 1.9–2.7 (8H, m).

(2) 4l-(4-Pyridyl)pimelic acid methyl ester

Into 250 ml of concentrated hydrochloric acid, 13 g of 4-cyano-4-(4-pyridyl)pimelic acid methyl ester was dissolved, and the solution was refluxed for 14 hours. Hydrochloric acid was distilled off under reduced pressure and the residue was dissolved in 200 ml of methanol. To this solution, there was added 1 ml of concentrated sulfuric acid and the mixture was refluxed for 4 hours. After 3 g of sodium bicarbonate was added, methanol was distilled off and 150 ml of water and 150 ml of ethyl acetate were added. Further, 25 g of sodium bicarbonate was gradually added. The organic layer was removed, washed with 50 ml of saturated aqueous solution of sodium chloride, and dried over anhydrous sodium sulfate. After the solvent was distilled off, there was obtained 26 g of 4-(4-pyridyl)pimelic acid methyl ester as an oily material.

IR(Neat): 2950, 1740, 1600, 1435, 1250, 1200, 1170 cm$^{-1}$

NMR(100 MHz, CCl$_4$, δ): 8.6 (2H, m); 7.4 (2H, m); 3.58 (6H, s); 2.55 (1H, m); 1.7–2.28 (8H, m).

(3) 2-Methoxycarbonyl-4-(4-pyridyl)cyclohexanone

To 100 ml of tetrahydrofuran, there was added 13 g of potassium t-butoxide. A solution of 26 g of 4-(4-pyridyl)pimelic acid methyl ester in 50 ml of tetrahydrofuran was added at 20° to 40° C. and the mixture was stirred for 2 hours. After the reaction was completed, the mixture was treated with saturated aqueous solution of ammonium chloride and then extracted with ether. The ether solution was washed with water and dried. Ether was distilled off and the residue was recrystalized from ether. There was obtained 9.6 g of 2-methoxycarbonyl-4-(4-pyridyl)cyclohexanone: m.p. 82°–83° C.

IR(KBr): 2940, 1730, 1650, 1620, 1610, 1440, 1230 cm$^{-1}$

NMR(100 MHz, CDCl$_3$, δ): 12.18 (1H, s); 8.5–8.64 (2H, m); 7.12–7.28 (2H, m); 3.76 (3H, s); 1.6–2.5 (7H, m).

What is claimed is:

1. 2-Methoxycarbonyl-4-(4-pyridyl)cyclohexanone.
2. Ethoxycarbonyl-4-(4-pyridyl) cyclohexanone.

* * * * *